United States Patent
Berube et al.

(12)

(10) Patent No.: US 6,479,442 B1
(45) Date of Patent: Nov. 12, 2002

(54) HYDROTROPE AND SKIN CONDITIONING AGENTS FOR USE IN LIQUID DETERGENT COMPOSITIONS

(75) Inventors: Robert G. Berube, Newtown, PA (US); Ernest H. Brumbaugh, Rockford, MI (US); Robert D. Faber, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 09/674,987
(22) PCT Filed: May 5, 1999
(86) PCT No.: PCT/US99/09936
§ 371 (c)(1),
(2), (4) Date: Dec. 11, 2000
(87) PCT Pub. No.: WO99/57234
PCT Pub. Date: Nov. 11, 1999

(51) Int. Cl.⁷ .............................. C11D 1/72; C11D 1/825
(52) U.S. Cl. .................. 510/159; 510/422; 514/723
(58) Field of Search .................. 510/235, 236, 510/237, 340, 341, 422, 423, 424, 425, 537, 497, 159; 514/723

(56) References Cited

U.S. PATENT DOCUMENTS

| 5,422,112 A | * | 6/1995 | Williams | 424/401 |
| 5,561,106 A | * | 10/1996 | Erilli et al. | 510/109 |
| 5,589,177 A | * | 12/1996 | Herb et al. | 424/401 |
| 5,656,280 A | * | 8/1997 | Herb et al. | 424/401 |
| 5,814,662 A | * | 9/1998 | Znaiden et al. | 514/557 |

FOREIGN PATENT DOCUMENTS

WO    WO 97/18284    *  5/1997

* cited by examiner

Primary Examiner—John Hardee
(74) Attorney, Agent, or Firm—Alticor Inc.

(57) ABSTRACT

Liquid detergent compositions containing from about 1% to about 90% of a surfactant selected from anionic, nonionic, and amphoteric surfactants and mixtures thereof are prepared with a hydrotrope that is a mixture of an alcohol ethoxylate and a polyethylene glycol ether of glycerin. The hydrotrope provides increased foam generation. The use of a polyethylene glycol ether of glycerin and an alpha hydroxy acid in a liquid detergent composition further promotes skin improvement and maintains healthy skin of the person using the detergent.

12 Claims, 6 Drawing Sheets

HYDROTROPE AND SKIN CONDITIONING AGENTS FOR USE IN LIQUID DETERGENT COMPOSITIONS

TECHNICAL FIELD

The present invention relates to an improved hydrotrope for liquid detergent compositions. In particular, the invention relates to a novel and synergistic hydrotrope that is a combination of a polyethylene glycol ether of glycerin and an alcohol ethoxylate and is useful for surfactant based detergent compositions. The invention further relates to the use of a polyethylene glycol ether of glycerin and an alpha hydroxy acid in a liquid detergent composition, which synergistically combine to provide skin conditioning benefits to the user of the liquid detergent composition.

BACKGROUND ART

Liquid detergent compositions are used in a variety of cleaning activities. For example, they are used to machine wash and hand wash clothes, dishes, hard surfaces such as walls and glass, and automotive surfaces. Generally, each use dictates different desired performance characteristics for each type of detergent composition. For example, it is desired that liquid detergents used to machine wash clothes or dishes do not generate a high volume of foam because excessive foam can inhibit cleaning efficacy and be difficult to remove from the washing machine. On the other hand, it is desired that a detergent composition used to hand wash clothes, dishes, or automobiles (and similar vehicles) generate foam because the perception of cleaning quality is directly related to foam volume in these applications.

At the same time, the detergent composition; should be easily dispersed, particularly when incorporated in an aqueous carrier, and have an appropriate viscosity, i.e., be free from gelling. To accomplish these and other objectives, it is known to add hydrotropes; for example an alcohol such as ethanol. Unfortunately, the use of ethanol raises flammability concerns and also tends to produce compositions that develop a surface skin on standing ,because of evaporation of the volatile components of the detergent concentrate. Moreover, if more than a minimal amount of ethanol is required to prevent gelling, the. compositions may impart the typical odor of ethanol that is difficult to cover with fragrances.

Thus, there is always a need for a detergent composition that satisfies a variety of performance characteristics such as foam generation, dispersability and viscosity control, compatibility with other formulation components, environmental safety and cost effectiveness.

The present invention provides such a composition by providing a novel hydrotrope that results in liquid detergents that have excellent dispersability, gelling/viscosity, odor and foaming characteristics. The novel hydrotrope is a combination of a polyethylene glycol ether of glycerin and an alcohol ethoxylate that synergistically provides improved performance characteristics beyond that which would be expected from their additive effects.

Another common problem associated with the use of liquid detergent compositions is the negative health effects to the user's skin that may result from frequent washing activities and/or exposure to the detergent. Typical negative health effects include dryness, redness, flaking, and irritation of the skin. Ideally, it would be desirable to provide a liquid dishwashing composition that is both effective in cleaning the desired article as well as being mild to the skin and help to maintain or improve healthy skin.

DISCLOSURE OF THE INVENTION

According to the present invention, a liquid detergent composition is provided that comprises from about 1% to about 90% of a main detergent surfactant and from about 1% to about 40% of a hydrotrope that is a combination of a polyethylene glycol ether of glycerin and a short-chain alcohol ethoxylate. The liquid detergent preferably is an aqueous detergent and thus can coritain from about 1% to about 90% water. Nevertheless, it is desirable to provide a concentrated composition and, thus, the detergent preferably contains from about 1% to about 40% water.

In another embodiment of the present invention, a liquid detergent composition is provided that comprises from about 1% to about 90% of a main detergent surfactant, from about 1% to about 400/% of a hydrotrope that is the combination of a polyethylene glycol ether of glycerin and a short-chain alcohol ethoxylate, and from about 0.01% to about 1.5% of a hydroxy carboxylic acid.

The main detergent surfactant includes at least one surfactant selected from the group consisting of anionic, nonionic, amphoteric surfactants and mixtures thereof. The anionic surfactant includes but is not limited to the sulfated anionic surfactants, sulfonated anionic surfactants, sulfosuccinates, sulfosuccinamates, taurates, isethionates, salts of fatty acids, carboxylated alcohol ethoxylates, ether sulfates and combinations thereof. The nonionic surfactant includes but is not limited to the alkanolamides, amine oxides, alkoxylated alcohols, alkoxylated phenols, block polymers and co-polymers, alkoxylated amines, alkyl polysaccharides, glucosamides, sugar esters and combinations thereof. The amphoteric surfactant includes but is not limited to the; monoacetates, diacetates, betaines, glycinates, imidazolines, imidazoline derivatives, monopropionates, dipropionates, hydroxy sultaines and combinations thereof.

Foam-enhancing agents may be added to the composition and, if added, are present in an amount from about 1% to about 40%. Although the foam-enhancing agent may be the same as one or more of the surfactants included as part of the main surfactant, typically the foam-enhancing agent will be different. The foam-enhancing agent is typically selected from the group consisting of amine oxides, amides, alkyl glucosides, fatty alcohols, and mixtures thereof.

The hydrotrope of the present invention can be used in conjunction with or to replace in whole or in part these foam-enhancing surfactants. Preferably, the hydrotrope of the present invention is used in conjunction with these foam-enhancing surfactants. In this instance, the presence of the hydrotrope of the present invention provides foam generation greater than without the presence of the novel hydrotrope.

In addition, the hydrotrope of the present invention can be used to replace in whole or in part the known hydrotropes such as the alcohols, diols, and triols. Generally, the weight ratio of the polyethylene glycol ether of glycerin to the short-chain alcohol ethoxylate ranges from about 1:20 to about 20:1, preferably from about 1:10 to about 10:1, and more preferably from about 1:3 to about 3:1.

In one embodiment, the hydrotrope consists of a mixture of a polyethylene glycol ether of glycerin and a short-chain alcohol ethoxylate where they are the only added hydrotrope constituents present in the composition. In this regard, it is known that some surfactants such as ether sulfates, when commercially supplied, contain low molecular weight alcohols, such as ethanol, which if added to a detergent composition may be considered a hydrotrope. These low molecular weight alcohols are incorporated in the commercial products so that they are free-flowing liquids. Thus, in this embodiment, when it is stated in the specification and claims that the hydrotrope consists of a mixture of a polyethylene glycol ether of glycerin and a short-chain alcohol ethoxylate where they are the only added hydrotrope constituents present, it is meant to exclude any added alcohol, diol, or polyol as a hydrotrope, but is not meant to exclude low molecular Weight alcohol (e.g., ethanol) that may be present as part of the surfactant constituent. Thus, it is not meant to exclude any ethanol that is present in a commercially available surfactant such as an ether sulfate.

In one preferred embodiment of the present invention, a liquid detergent is provided that consists essentially of from about 1% to about 90% of one or more anionic surfactants, from about 1% to about 40% of one or more foam-enhancing agents, and from about 1% to about 40% of a hydrotrope. The hydrotrope in this embodiment is a mixture of an alcohol ethoxylate and an ethoxylated glycerin such that the hydrotrope comprises from about 90% to about 100% of a mixture of an alcohol ethoxylate and an ethoxylated glycerin, preferably such that the hydrotrope comprises 100% of a mixture of an alcohol ethoxylate and an ethoxylated glycerin. In other words, the resulting composition is substantially free or completely free from other added hydrotropes (excluding those present! as a result of surfactant manufacturing such as ethanol present in commercially available ether sulfates).

In another embodiment of the present invention, a liquid detergent is provided that comprises from about 1% to about 90% of a main detergent surfactant selected from the group consisting of anionic, nonionic, amphoteric surfactants, and mixtures thereof and from about 1% to about 40% of a hydrotrope wherein the hydrotrope comprises at least about 50% of a mixture of a polyethylene glycol ether of glycerin and a short-chain alcohol ethoxylate. In this embodiment, the main detergent surfactant is preferably selected from the group consisting of anionic and nonionic surfactants, and mixtures thereof. More preferably, the main detergent surfactant comprises predominantly one or more nonionic surfactants with the balance being one or more anionic surfactants. For example, the main detergent surfactant comprises from about 50% to about 90% of one or more nonionic surfactants and from about 10% to about 50% of one or more anionic surfactants.

The present invention is also directed to an, improved liquid detergent composition containing one or more surfactants selected from the group consisting of anionic, nonionic, amphoteric surfactants, and mixtures thereof, wherein the improvement comprises an effective amount of a hydrotrope to provide increased foam generation ability to the composition and wherein the hydrotrope comprises a mixture of an alcohol ethoxylate and an ethoxylated glycerin.

The present invention also includes a method of increasing the foam generation ability of a liquid detergent composition that comprises the step of adding an effective amount of a hydrotrope to the liquid detergent wherein the liquid detergent includes one or more surfactants selected from the group consisting of anionic, nonionic, amphoteric surfactants and mixtures thereof and wherein the hydrotrope is a mixture of an alcohol ethoxylate and an ethoxylated glycerin.

It is noted that, unless otherwise stated, all percentages given in this specification and the appended claims refer to percentages by weight.

MODES FOR CARRYING OUT THE INVENTION

Figure 1:
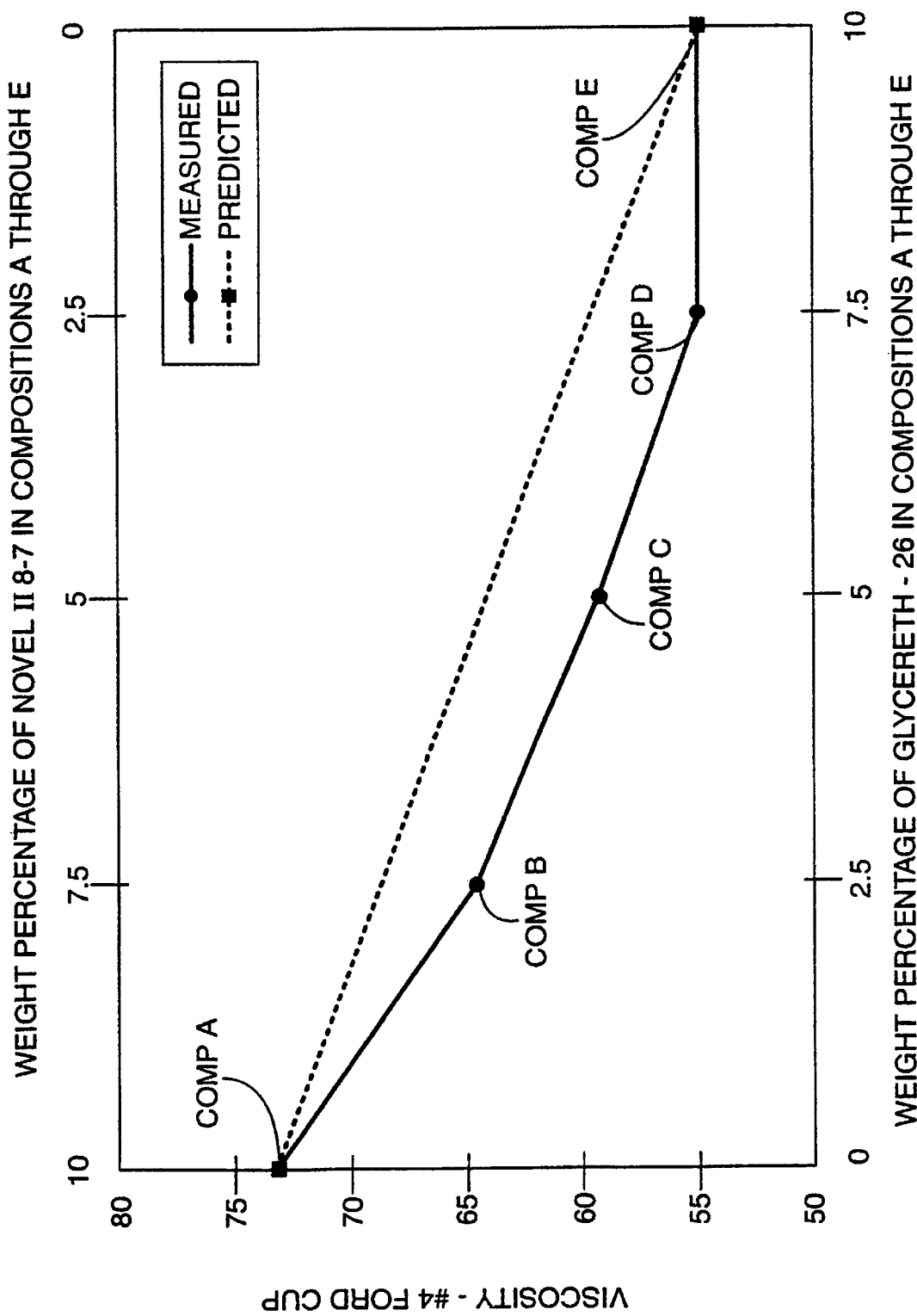
FIG. 1 shows the viscosity of a liquid detergent that includes a hydrotrope according to one embodiment of the present invention, i.e., the combination of a polyethylene glycol ether of glycerin and a short-chain alcohol ethoxylate at various ratios. The graph demonstrates that the presence of the: hydrotrope according to the present invention results in a product that has a lower viscosity than would be expected by the additive effect of each of the hydrotrope constituents.

In accordance with the present invention, a liquid detergent composition contains from about 1% to about 90% of a main surfactant selected from the group consisting of anionic, nonionic, and amphoteric surfactants, and mixtures thereof; and from about 1% to about 40% of a hydrotrope comprising a mixture of an alcohol ethoxylate and a polyethylene glycol ether of glycerin. As used herein, the term "hydrotrope" is generally defined as any substance, or combinations of substances, which increase the solubility in water of another substance, which is only partially soluble in water.

In one embodiment of the present invention, the hydrotrope comprises at least about 50% of a mixture of an alcohol ethoxylate and a polyethylene glycol ether of glycerin. In another embodiment of the present invention, the hydrotrope comprises from about 90% to about 100%, preferably 100% of a mixture of an alcohol ethoxylate and a polyethylene glycol ether of glycerin.

The main surfactant includes anionic, nonionic, amphoteric surfactants, and mixtures thereof. The surfactants useful in the detergent composition include, but are not limited to, those listed and described in "Surface Active Agents and Detergents" Volumes I and II by Schwartz, Perry & Berch, in "Nonionic Surfactants" by M. J. Schick, and in McCutcheon's "Emulsifiers & Detergents", each of which are incorporated herein by reference.

Typically, the liquid detergent contains a sufficient amount of main surfactant to provide desired cleaning performance. Accordingly, the liquid detergent contains from about 1% to about 90% of the main surfactant. Preferably, the liquid detergent contains from about 10% to about 80% of the main surfactant, more preferably from about 15% to about 70%, particularly from about 20% to about 60% of the main surfactant.

Useful anionic surfactants include the water-soluble salts of the higher fatty acids, i.e., soaps. This includes alkali metal soaps such as the sodium, potassium, ammonium, alkyl ammonium, and alkanol ammonium salts of higher fatty acids containing from about 8 to about 24 carbon atoms. Soaps can be made by direct saponification of fats and oils or by the neutralization of free fatty acids. Particularly useful are the sodium, ammonium, and potassium salts; of fatty acids. For example, the ammonium salt of oleic acid formed by neutralization with triethanolamine.

Useful anionic surfactants also include the water-soluble salts, preferably the alkali metal, ammonium and alkylolammonium salts, of: reaction products of organic compounds and sulfur containing compounds having in their molecular structure an alkyl group containing from about 8 to about 20 carbon: atoms and a sulfonic acid or sulfuric acid ester group. Included in the term "alkyl" is the alkyl portion of acyl groups. Examples of this group of synthetic surfactants are the ammonium, alkanolammonium, alkanolamine, sodium, and potassium alkyl sulfates, especially those obtained by sulfating the higher primary or secondary alcohols ($C_8$–$C_{18}$ carbon atoms) such as those produced by reducing the glycerides of tallow or coconut oil; isethionates, and the ammonium, sodium, and potassium alkylbenzene sulfonates in, which the alkyl group contains from about 10 to about 16 carbon atoms, in straight chain or branched chain configuration, e.g., see U.S. Pat. No. 2,220,099 and alkylbenzene sulfonates in which the average number of carbon atoms in the alkyl group is from about 11 to 14, abbreviated as $C_{11-14}$ LAS.

The anionic surfactants useful in the present invention may also include the potassium, sodium, calcium, magnesium, ammonium or lower alkanolammonium, such as triethanolammonium, monoethanolammonium, or diisopropanolammonium paraffin or olefin sulfonates in which the alkyl group contains from about 10 to about 20 carbon atoms. The lower alkanol of such alkanolammonium will normally be of 2 to 4 carbon atoms and is preferably ethanol. The alkyl group can be straight or branched and, in addition, the sulfonate is preferably joined to any secondary carbon atom, i.e., the sulfonate is not terminally joined.

Other anionic surfactants that may be useful in the present invention include secondary alkyl sulfates having the general formula

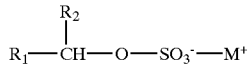

wherein M is ammonium, potassium, sodium, calcium, magnesium, or other suitable cations, $R_1$ represents an alkyl group having from about 3 to about 18 carbon atoms and $R_2$ represents an alkyl group having from about 1 to about 6 carbon atoms. Preferably, M is sodium, $R_1$ is an alkyl group having from about 10 to about 16 carbon atoms, and $R_2$ is an alkyl group having from about 1 to about 2 carbon atoms.

Other anionic surfactants useful herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl group contains from about 10 to about 20 carbon atoms.

Other useful anionic surfactants include the water-soluble salts of esters of alpha-sulfonated fatty acids containing from about 6 to 20 carbon atoms in the fatty acid group and from about 1 to 10 carbon atoms in the alcohol group; water-soluble salts of 2-acyloxyalkane-1-sulfonic acids containing from about 2 to 9 carbon atoms in the acyl group and from about 9 to about 23 carbon atoms in the alkane moiety; water-soluble salts of olefin and paraffin sulfonates containing from about 12 to 20 carbon atoms; and beta-alkyloxy alkane sulfonates containing from about 1 to 3 carbon atoms in the alkyl group and from about 8 to 20 carbon atoms in the alkane moiety. For example, an alpha sulfomethyl cocoate may be useful in one or more embodiments of the present invention.

Another example of anionic surfactants that may be useful in the present invention are those compounds which contain two anionic functional groups. These are referred to as di-anionic surfactants. Suitable di-anionic surfactants are the disulfonates, disulfates, or mixtures thereof which may be represented by the following formulas:

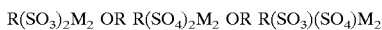

where R is an acyclic aliphatic hydrocarbyl group having 15 to 20 carbon atoms and M is a water-solubilizing cation, for example, the $C_{15}$ to $C_{20}$ dipotassium-1,2-alkyldisulfonates or disulfates, disodium 1,9-hexadecyl disulfates, $C_{15}$ to $C_{20}$ disodium 1,2-alkyldisulfonates, disodium 1,9-stearyldisulfates and 6,10-octadecyidisulfates.

Anionic surfactants containing a carboxyl group may also be used in the detergent composition and include, but are not limited ,to, salts of fatty acids, and carboxylated alcohol ethoxylates. Particular examples of these types of anionic surfactants are described in McCutcheon's.

Preferred anionic surfactants include those having at least one sulfur constituent. Such anionic surfactants include the sulfated and sulfonated anionic surfactants. Examples of such include, but are not limited to primary and secondary alkyl sulfates, primary and secondary sulfates of ethoxylated alcohols and acids, sulfates of fatty esters, ether sulfates (i.e., alcohol ethoxy sulfates), alkenyl carboxysulfonates, methyl ester sulfonates, linear alkylbenzene sulfonates, alpha olefin sulfonates, sulfonates of dodecyl benzene, sulfonates of tridecylbenzene, primary and secondary alkyl sulfonates, sulfonates of naphthalene and alkyl naphthalene, and sulfonates of petroleum, sarcosinates, sulfosuccinamates, sulfosuccinates and taurates.

The particularly preferred anionic surfactants for one embodiment of the present invention (i.e., where the main surfactant comprises a major amount of an anionic surfactant) are the ether sulfates such as the. polyoxyethylene alkyl ether sulfates and tridecyl ether sulfates, alkyl ether sulfates derived from natural alcohols such as sodium lauryl alcohol polyglycol ether sulfates and fatty alcohol ether sulfates, alkyl ether sulfates derived from synthetic alcohols, such as sodium lauryl ether sulfate, sodium myristyl ether sulfate, polyoxyethylene lauryl ether sulfate, triethanolamine lauryl ether sulfate, and ammonium laurel ether sulfate.

Accordingly, the ether sulfates useful in the present invention are those having the formula $RO(C_2H_4O)_xSO_3M$ wherein R is alkyl or alkenyl having from about 8 to about 20 carbon atoms, x is 1 to 30, and M is a water-soluble cation, preferably sodium, ammonium, and potassium. Preferably, R has 10 to 16 carbon atoms. The alcohols can be derived from natural fats, e.g., coconut oil or tallow, or can be synthetic. Such alcohols are reacted with 1 to 30, and especially 1 to 12, molar proportions of ethylene oxide and the resulting mixture of molecular species is sulfated and neutralized.

Typically, the commercially supplied ether sulfates contain less than 100% active ether sulfate product and, to supply a free-flowing product, they contain a lower molecular weight alcohol to reduce the viscosity so that the surfactant can be poured. The amount of alcohol varies and can be from about 10% to about 15% of the supplied product. Although this alcohol is present, those of skill in the art do not consider it to comprise any or a portion of the added hydrotrope. Thus, the term "hydrotrope" as used in the specification and claims, does not include the alcohol present as a part of the surfactant such as an ether sulfate.

In addition, when the specification describes and the claims limit the hydrotrope such that the hydrotrope comprises from about 90% to about 100% of a mixture of an alcohol ethoxylate and an ethoxylated glycerin, preferably such that the hydrotrope comprises 100% of a mixture of an, alcohol ethoxylate and an ethoxylated glycerin mixture, such description is meant to exclude any added alcohol, diol, or polyol as a hydrotrope for the composition, as a whole. It is not meant to exclude any alcohol typically present in commercially available surfactants as a result of processing.

Examples of nonionic surfactants include, but are not limited to, compounds produced by the condensation of alkylene oxide groups (hydrophilic in nature) with an organic hydrophobic compound, which may be aliphatic or alkyl aromatic in nature. The length of the polyoxyalkylene group which is condensed with any particular hydrophobic group can be readily adjusted to yield a water-soluble compound having the desired degree of balance between hydrophilic and hydrophobic elements.

For example, the nonionic surfactants may include the polyoxyethylene or polyoxypropylene condensates of aliphatic carboxylic;: acids, whether linear or branched chain and unsaturated or saturated, containing from about 8 to about 18 carbon atoms in the aliphatic chain and incorporating from about 5 to about 50 ethylene oxide or propylene oxide units. Suitable carboxylic acids include "coconut" fatty acid which contains an average of about 12 carbon atoms, "tallow" fatty acid which contains an average of about 18 carbon atoms, palmitic acid, myristic acid, stearic acid, and lauric acid.

The nonionic surfactants can also include polyoxyethylene or polyoxypropylene condensates of aliphatic alcohols, whether linear or branched chain and unsaturated or saturated, containing from about 8 to about 24 carbon atoms and incorporating from about 5 to about 50 ethylene oxide or propylene oxide units. Suitable alcohols include the coconut fatty alcohol, tallow fatty alcohol, lauryl alcohol, myristyl alcohol, and oleyl alcohol.

Examples include those having the formula $R(OC_2H_4)_nOH$, where R is a $C_8$–$C_{16}$ alkyl group or a $C_8$–$C_{12}$ alkyl phenyl group, and n is from 3 to about 80. Particularly preferred nonionic surfactants are the condensation products of $C_{12}$–$C_{16}$ alcohols with from about 5 to about 20 moles of ethylene oxide per mole of alcohol, e.g., a $C_{12}$–$C_{15}$ alcohol condensed with about 6 to about 9 moles of ethylene oxide per mole of alcohol. Nonionic surfactants of this type include the NEODOL® brand products, e.g., Neodol 23-6.5, Neodol 25-7, Neodol 25-9 which are, respectively, $C_{12\text{-}13}$ linear primary alcohol ethoxylate having 6.5 moles of ethylene oxide, $C_{12\text{-}15}$ linear primary alcohol ethoxylate having 7 moles of ethylene oxide, and $C_{12\text{-}15}$ linear primary alcohol ethoxylate having 9 moles of ethylene oxide.

Alkyl saccharides may also find use in the composition. In general, the alkyl saccharides are those having a hydrophobic group containing from about 8 to about 20 carbon atoms, preferably from about 10 to about 16 carbon atoms, and a polysaccharide hydrophilic group containing from about 1 (mono) to about 10 (poly), saccharide units (e.g., sucrose, galactoside, glucodside, fructoside, glucosyl, fructosyl, and/or galactosyl units). Mixtures of saccharide moieties may be used in the alkyl saccharide surfactants. Preferably, the alkyl: saccharides are the alkyl glucosides having the formula:

$$RO(C_nH_{2n}O)_t(Z)_x$$

wherein Z is derived from glucose, R is a hydrophobic gro:up selected from the group consisting of alkyl, alkylphenyl, hydroxyalkyl, hydroxyalkylphenyl, and mixtures thereof in which the alkyl groups contain from about 10 to about 18 carbon atoms, n is 2 or 3, t is from 0 to about 10, and x is from 1 to about 8. Examples of such alkyl saccharides are described in U.S. Pat. No. 4,565,647 (at col. 2, line 25 through col. 3, line 57) and U.S. Pat. No. 4,732,704 (at col. 2, lines 15–25), the pertinent portions of each are incorporated herein by reference.

Semi-polar nonionic surfactants include water-soluble amine oxides containing one alkyl moiety of from about 10 to 18 carbon atoms and two moieties selected from the group of alkyl and hydroxy alkyl moieties of from about 1 to about 3 carbon atoms; water-soluble phosphine oxides containing one alkyl moiety of about 10 to 18 carbon atoms and two moieties selected from the group consisting of alkyl groups and hydroxy alkyl groups containing from about 1 to 3 carbon atoms; and water-soluble sulfoxides containing one alkyl moiety of from about 10 to 18 carbon atoms and a moiety selected from the group consisting of alkyl and hydroxy alkyl moieties of from about 1 to 3 carbon atoms.

Amphoteric surfactants that may be useful in the detergent composition include, but are not limited to, mono- and diacetates, betaines, glycinates, imidazolines and their derivatives, mono- and dipropionates, and hydroxy sultaines.

Desirably, the liquid detergent contains one or more foam-enhancing agents. These agents are added to enhance the foam generating capability of the main surfactants to provide a desirable amount of foam. Oftentimes, users of liquid detergents perceive the presence of foam to indicate the cleaning performance of a detergent. Accordingly, foam-enhancing agents are preferably added to the liquid detergent compositions of the present invention.

The foam-enhancing agents may include one, or more of the nonionic surfactants described above. Preferably, the foam enhancing agent is selected from the group consisting of amides, amine oxides, alkyl glucosides (e.g., those described above), fatty alcohols, and mixtures thereof. More preferably, the foam enhancing agent is selected from the group consisting of amides and amido amine oxides.

Examples of suitable amides include, but are not limited to, the ammonia, monoalkanol, and dialkanol amides of fatty acids having an acyl moiety of from about 8 to about 18 carbon atoms where the alkanol has from 2 to 4 carbon atoms and is generally represented by the formula:

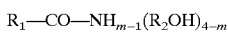

$$R_1-CO-NH_{m-1}(R_2OH)_{4-m}$$

wherein $R_1$ is a saturated or unsaturated aliphatic hydrocarbon radical having from 8 to 18, preferably from 12 to 14 carbon atoms; $R_2$ is a methylene, ethylene, or propylene group; and m is 1, 2, 3 or 4 preferably 1 or 2, more preferably 1.

Suitable examples include but are not limited to the mono and di-ethanol coconut, lauric, and myristic fatty acid amides. The acyl moities may be derived from naturally occurring glycerides, e.g., coconut oil, palm oil, soybean oil, and tallow, but can be derived synthetically, e.g., by the oxidation of petroleum or hydrogenation of carbon monoxide by the Fischer-Tropsch process.

The amine oxides include the alkyl amine oxides and the amido amine oxides. The alkyl amine oxides are described above. The amido amine oxides include those having the formula:

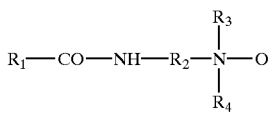

wherein $R_1$ is a $C_{8-18}$ alkyl, $R_2$ is a $C_{2-4}$ alkyl, and $R_3$ and $R_4$ are a $C_{1-5}$ alkyl or hydroxyalkyl. Preferably, $R_1$ is a $C_{12-14}$ alkyl, $R_2$ is ethyl or propyl and $R_3$ and $R_4$ are methyl or ethyl.

Suitable examples include but are not limited to babassuamidopropyl amine oxide, cocamidopropyl amine oxide, isostearylamidopropyl amine oxide, isostearylamidopropoyl morpholine oxide, lauraniidopropyl amine oxide, lauric/myristic amidopropyl amine oxide, minkamidopropyl amine oxide, oleoamidopropyl amine oxide, stearamidopropyl amine oxide, and wheat germ amidopropyl amine oxide. A particularly preferred amido amine oxide is one where $R_1$ is a $C_{12}$ alkyl, $R_2$ is propyl, and $R_3$ and $R_4$ are methyl.

The foam enhancing agent is typically added to the liquid detergent in an amount from about 1% to about 40%, preferably from about 1% to about 35%, more preferably from about 2% to about 35%, and most preferably from about 3% to about 30%.

The hydrotrope comprises a mixture of an alcohol ethoxylate and a polyethylene glycol ether of glycerin. Surprisingly, it has been found that a mixture of these constituents provide foam generation greater than that which would be expected from the additive effects of each constituent. In addition, the mixture provides decreased viscosity and quicker dissolution than, would be expected.

Although it is known that certain alcohol ethoxylates can provide foam-enhancing properties to an anionic surfactant based detergent, it is surprising that a polyethylene glycol ether of glycerin, i.e., an ethoxylated glycerin, would provide any foam-enhancing benefits in conjunction with its hydrotrope properties. Even more surprising is the finding that a mixture of an ethoxylated glycerin and an alcohol ethoxylate provides a synergistic foam-enhancing result.

The ethoxylated alcohol nonionic surfactant useful,: for the hydrotrope may be the same as that added as part of the detergent composition. Accordingly, any ethoxylated alcohol having the formula $R(OC_2H_4)_nOH$, where R is a $C_6-C_{18}$ alkyl group or a $C_6-C_{12}$ alkyl phenyl group, and n is from 3 to about 80 is suitable for use in this invention. Short-chain ethoxylated alcohols, i.e. an alcohol where R is an alkyl group or alkyl phenyl group having less than 12 carbon atoms, are preferred.

Particularly preferred are the condensation products of $C_6-C_{12}$ alcohols with from about 3 to about 20 moles of ethylene oxide per mole; of alcohol, e.g., a $C_6-C_{12}$ alcohol condensed with about 3 to about 15 moles of ethylene oxide per mole of alcohol. More preferably, the ethoxylated alcohol is a $C_6-C_{10}$ alcohol with from about 3 to about 9 moles of ethylene oxide per mole of alcohol. It is preferred to use those alcohol ethoxylates with a narrow-range distribution such as those commercially available under the NOVEL® II trade name. These are generally referred to as peaked alcohol ethoxylates and are preferred because they contain only a small amount of free short-chain fatty alcohols and, as a result do not impart to the composition the characteristic unpleasant odor associated with short-chain fatty alcohols. Accordingly, a particularly preferred alcohol ethoxylate is a peaked $C_8$ alcohol having an average of 7 moles of ethylene oxide.

The polyethylene glycol ether of glycerins useful as a hydrotrope in the present invention are those having the general formula

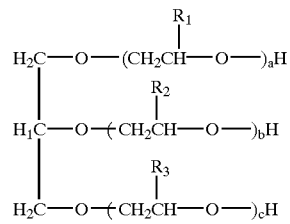

wherein a+b+c has an average value of from about 2 to about 60, preferably from about 10 to about 45, more preferably from about 20 to about 30 and wherein $R_1$, $R_2$, and $R_3$ may be the same or different and are selected from the group consisting of H, $CH_3$, or $C_2H_5$. A particularly preferred ethoxylated glycerin is Glycereth-26 (where a+b+c has an average value of about 26).

The polyethylene glycol ether of glycerin can be prepared by any suitable method including by the reaction of glycerin and ethylene oxide in presence of an alkaline catalyst such as KOH or NaOH.

The hydrotrope of the present invention is present: in the liquid detergent in an amount from about 1% to about 40%, preferably from about 1% to about 35%, more preferably from about 2% to about 35%, and most preferably from about 2% to about 30%.

According to one embodiment of the present invention, the hydrotrope is a mixture of an alcohol ethoxylate and an ethoxylated glycerin such that the mixture comprises at least about 50% of the hydrotrope. In this: one embodiment, the main surfactant is predominantly one or more nonionic surfactants.

In another embodiment of the present invention, the hydrotrope is a mixture of an alcohol ethoxylate and an ethoxylated glycerin such that the hydrotrope comprises from about 90% to about 100% of a mixture of an alcohol ethoxylate and an ethoxylated glycerin, preferably such that the hydrotrope comprises 100% of a mixture of an alcohol ethoxylate and an ethoxylated glycerin. In this embodiment, the main surfactant is predominantly one or more anionic surfactants and preferably is selected from one or more anionic surfactants.

The detergent compositions may contain other optional ingredients that may be typically found in liquid detergent compositions so long as they do not detract from the beneficial properties of the inventive hydrotrope. The compositions can contain from about 0.01% to about 10% of these optional ingredients and preferably no more than about 10%.

For example, the detergent composition may contain one or more acidifying agents, alkalinity sources, pH buffering agent, pH; control agents, and skin conditioning agents. Examples of acidifying agents include, but are not limited to, citric acid, glycolic acid, acetic acid, benzoic acid, phenol and palmitic acid. Examples of pH control agents include, but are not limited to, alkali metal carbonates and bicarbonates, monoethanolamine, triethanolamine, tris hydroxy methylamine, ammonium hydroxide, alkaline metal earths, and alkali metal hydroxides. The mono-, di-, and triethanolamines are preferred and can be added in an amount from about 0.01% to about 5%. Examples of skin conditioning agents include, but are not limited to, carboxylic hydroxy acids such as citric acid and lactic acid, moisturizers such as aloe vera gel, and any number of herbs, vitamins, minerals or other complexes having anti-oxidant, anti-inflammatory, and/or anti-aging activity such as Vitamins A, C, and E, algae, and licorice extract.

Builders may also be added, although they have limited value in some liquid detergent compositions such as hand dishwashing detergents. Either inorganic or organic builders may be used alone or in combination with themselves. Examples of such builders include but are not limited to alkali metal carbonates, phosphates, polyphosphates, and silicates.

Sequestrants can also be incorporated into the compositions. Examples of sequestrants include but are not limited to the alkali metal polycarboxylates, such as sodium and potassium citrate, sodium and potassium tartrate, citric acid, sodium and potassium ethylene diaminetetraacetate (EDTA), triacetates, sodium and potassium nitrilotriacetates (NTA), and mixtures thereof. These sequestrants can be used in amounts from about 0.01% to about 5%.

In addition, other optional ingredients including any of the usual adjuvants, diluents, and additives such as quaternary compounds, perfumes, enzymes, dyes, anti-tarnishing agents, antimicrobial agents, abrasives, water soluble salts of alkaline earth metals such as magnesium sulfate, and the like, can also be added provided that they do not detract from the advantageous properties of the compositions in accordance to the present invention.

The liquid detergent preferably is an aqueous detergent and thus can contain from about 1% to about 90% water. Nevertheless, it is desirable to provide a concentrated composition and, thus, the detergent preferably contains from about 1% to about 40% water.

In one preferred embodiment of the present invention, an aqueous detergent is provided that consists essentially of from about 1% to about 90% of one or more anionic surfactants, from about 1% to about 40% of a foam enhancing agent which is a mixture of an amido amine oxide and an alkyl diethanolamide, from about 1% to about 40% of a hydrotrope that consists of from about 90% to about 100%, preferably 100% of a mixture of an alcohol ethoxylate and an ethoxylated glycerin (polyethylene glycol ether of glycerin).

A particularly preferred embodiment of the present invention consists of from about 1% to about 90%, preferably from about 10% to about 70%, more preferably from about 15% to about 30% of a main surfactant consisting of a sodium alkyl ether sulfate, from about 1% to about 40%, preferably from about 5% to about 30%, and more preferably from about 10% to about 25% of a foam-enhancing agent selected from the group consisting of amido amine oxides, alkyl diethanol amides, and mixtures thereof; and from about 1% to about 40% of [ a] hydrotrope consisting of 100% of a mixture of an alcohol ethoxylate and an ethoxylated glycerin.

The alcohol ethoxylate is a $C_6$ to $C_{10}$ alcohol having an average of from about 3 to about 15 moles of ethylene oxide. Preferably, the alcohol ethoxylate is a peaked alcohol ethoxylate. More preferably, the alcohol ethoxylate is a peaked alcohol ethoxylate where the alcohol has about 8 carbon atoms and an average of 7 moles of ethylene oxide.

The ethoxylated glycerin has an average of from about 2 to about 60 moles of ethylene oxide, preferably from about 10 to about 45, more preferably from about 20 to about 30, and most preferably about 26 moles of ethylene oxide.

The ratio of the alcohol ethoxylate to ethoxylated glycerin is in the range of about 1:20 to about 20:1, preferably from about 1:10 to about 10:1, more preferably from about 1:3 to about 3:1.

In another preferred embodiment of the present invention, an aqueous detergent is provided that consists essentially of from about 1% to about 90% of a main surfactant selected from the group of anionic surfactants, nonionic surfactants, and mixtures thereof, and from about 1% to about 40% of a hydrotrope comprising at least about 50%, preferably at least about 60% and more preferably about 70% by weight of the hydrotrope of a mixture of an alcohol ethoxylate and ethoxylated glycerin. It will be understood that, in this embodiment, the composition may contain other hydrotropes such as sodium xylene sulfonate, alcohols such as ethanol, glycols such as propylene glycol, and alkoxylated alcohols, so long as at least about 50% of the hydrotrope includes the mixture of an alcohol ethoxylate and ethoxylated glycerin. In this embodiment, the main surfactant preferably includes from about 50% to about 90% by weight of the main surfactant, of one or more nonionic surfactants and from about 10% to about 50% by weight of the main surfactant of one or more anionic surfactants. The preferred ethoxylated alcohol and ethoxylated glycerin are the same as those described above. The ratio of alcohol ethoxylate to ethoxylated glycerin is in the range from about 1:20 to about 20:1, preferably from about 1:10 to about 10:1.

In another embodiment of the present invention, an aqueous detergent is provided that comprises from about 1% to about 90% of one or more anionic, nonionic, and amphoteric surfactants, or mixtures thereof, from about 1% to about 40% of a hydrotrope that is a mixture of an alcohol ethoxylate and an ethoxylated glycerin (polyethylene glycol ether of glycerin), and from about 0.01% to about 1.5% of a hydroxy carboxylic acid. Preferably, the ethoxylated glycerin has an average of from about 2 to about 60 moles of ethylene oxide, preferably from about 10 to about 45, more preferably from about 20 to about 30, and most preferably about 26 moles of ethylene oxide. Glycereth 26 is a preferred example of the ethoxylated glycerin. The hydroxy carboxylic acid suitable for use in this invention includes both alpha hydroxy acids and beta hydroxy acids. Preferably, the hydroxy carboxylic acid is an alpha hydroxy acid such as citric acid, malic acid, lactic acid, glycolic acid, tartartic acid, tartronic acid, and glucuronic acid. Citric acid is a preferred example of the alpha hydroxy acid. In a preferred embodiment, the liquid detergent includes about 5% Glycereth 26 and about 0.95% citric acid.

INDUSTRIAL APPLICABILITY

The hydrotrope and skin conditioning agents described herein may be used in any liquid detergent compositions. The hydrotrope and skin conditioning agents are particularly well suited for use in dishwashing, automotive washing, and other light duty washing compositions.

EXAMPLES

The following are illustrative examples of formulations and compositions according to this invention and it should be understood that they do not limit the scope of the invention:

Example 1

The following compositions were prepared:

TABLE 1

| Ingredient | A | B | C | D | E |
| --- | --- | --- | --- | --- | --- |
| Sodium lauryl ether sulfate (60% active) | 38.80 | 38.80 | 38.80 | 38.80 | 38.80 |
| Cocamide DEA (100% active) | 18.00 | 18.00 | 18.00 | 18.00 | 18.00 |
| Cocamidopropyl amine oxide (35% active) | 13.20 | 13.20 | 13.20 | 13.20 | 13.20 |
| Citric acid | 0.95 | 0.95 | 00.95 | 0.95 | 0.95 |
| Water | 19.05 | 19.05 | 19.05 | 19.05 | 19.05 |
| Ethoxylated Alcohol* (100% active) | 10.00 | 7.50 | 5.00 | 2.50 | 0.00 |
| Ethoxylated Glycerin** (100% active) | 0.00 | 2.50 | 5.00 | 7.50 | 10.00 |
| TOTAL | 100.00 | 100.00 | 100.00 | 100.00 | 100.00 |

*The ethoxylated alcohol was Novel II 8-7 (a peaked ethoxylated alcohol where the alcohol has about 8 carbon atoms and is ethoxylated with an average of 7 moles of ethylene oxide).
**The ethoxylated glycerin was a Glycereth-26.

Figure 2:
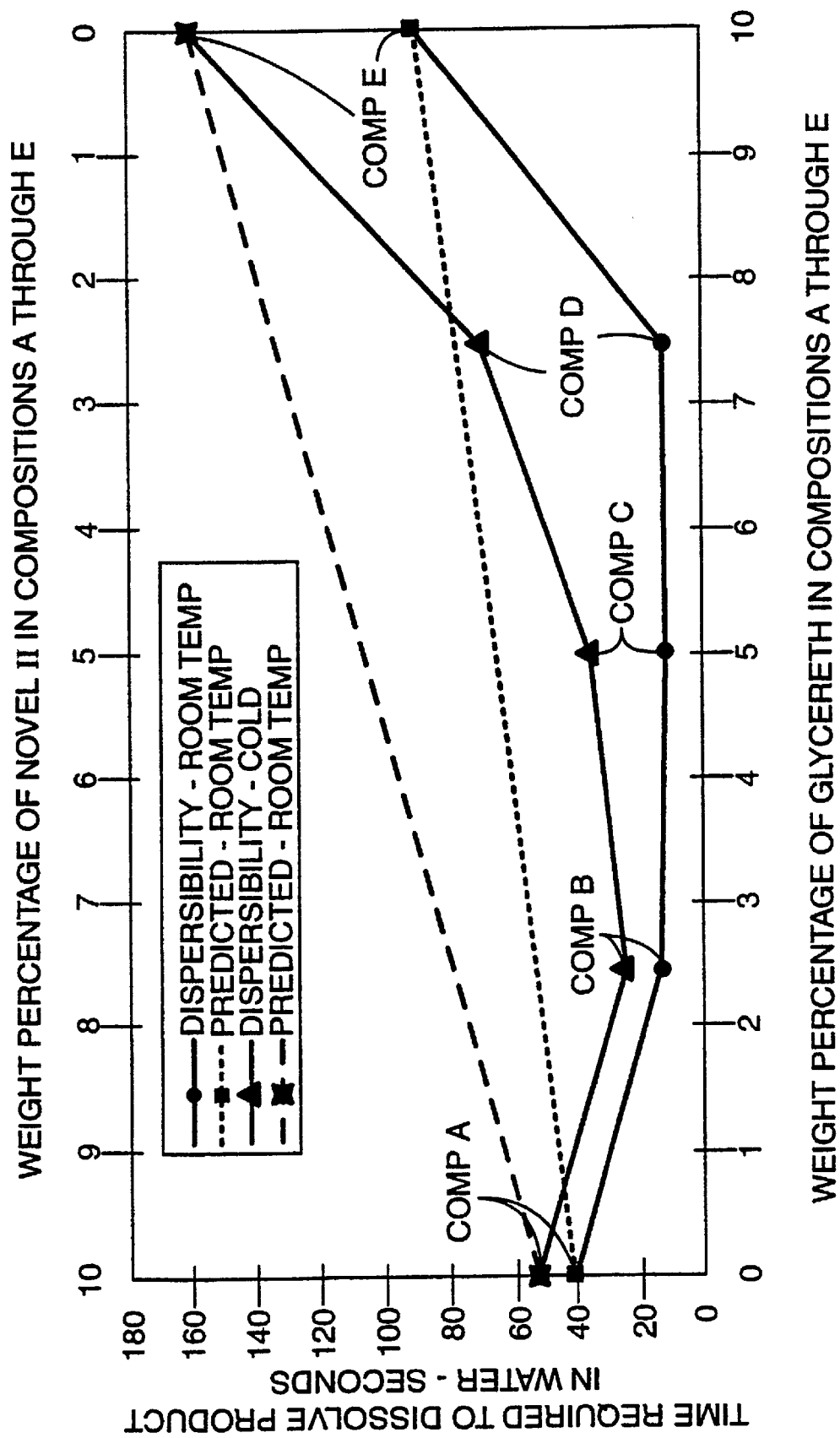
FIG. 2 shows the dissolution of a liquid detergent in water at room temperature and at 10° C. The liquid detergent includes a hydrotrope according to one embodiment of the present invention, i.e., the combination of a polyethylene glycol ether of glycerin and a short-chain alcohol ethoxylate at various ratios. The graph demonstrates that the presence of the hydrotrope according to the present invention results in a product that has better dissolution than would be expected by the additive effect of each of the hydrotrope constituents.
Figure 3:
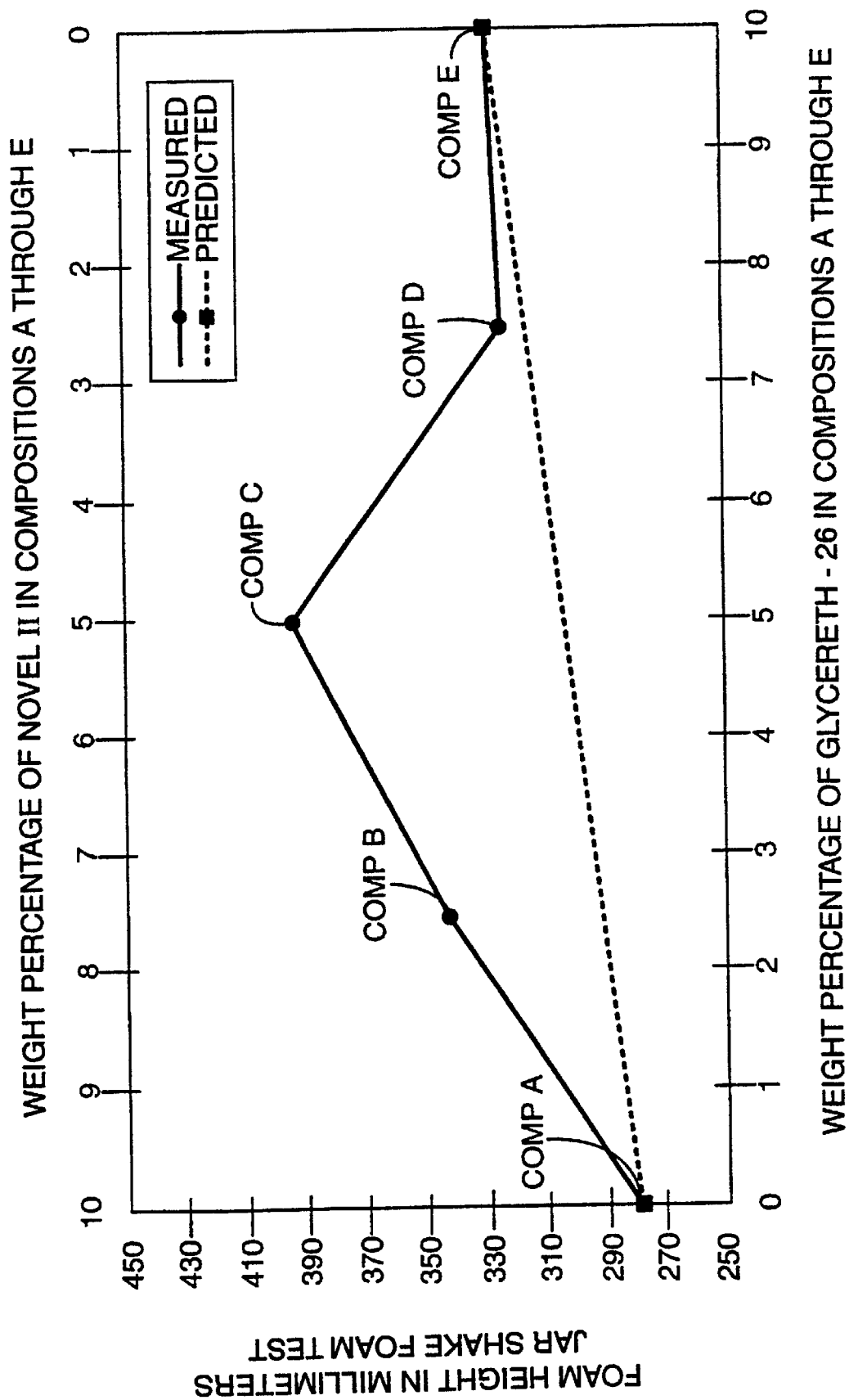
FIG. 3 shows the foam generation height of a liquid detergent that includes a hydrotrope according to one embodiment of the present invention, i.e., the combination of a polyethylene glycol ether of glycerin and short-chain alcohol ethoxylate at various ratios. The graph demonstrates that the presence of the hydrotrope according to the present invention results in a product that produces more foam than would be expected by the additive effect of each of the hydrotrope constituents.

Each of the compositions was tested to determine the effect of the hydrotrope of the present invention on product viscosity, product dispersability, and foam generation. FIG. 1 shows that compositions containing a mixture of the alcohol ethoxylate and ethoxylated glycerin decreased the product viscosity more than would have been expected from the additive effect of each of the constituents of the hydrotrope. FIG. 2 shows that compositions containing a mixture of the alcohol ethoxylate and ethoxylated glycerin dissolved faster in both room temperature water and in cold water than would have been expected from the additive effect of each of the constituents of the hydrotrope. FIG. 3 shows that compositions containing a mixture of the alcohol ethoxylate and ethoxylated glycerin generated more foam than would have been expected from the additive effect of each of the constituents of the hydrotrope.

Example 2

The following compositions were prepared:

TABLE 2

| Ingredient | F | G | H | I |
| --- | --- | --- | --- | --- |
| Sodium lauryl ether sulfate (60% active) | 42.00 | 42.00 | 42.00 | 42.00 |
| Cocamide DEA (100% active) | 12.00 | 12.00 | 12.00 | 12.00 |
| Cocamidopropyl amine oxide (35% active) | 10.00 | 10.00 | 10.00 | 10.00 |
| Citric acid | 0.68 | 0.68 | 0.68 | 0.68 |
| Triethanolamine | 0.50 | 0.50 | 0.50 | 0.50 |
| Water | 19.82 | 19.82 | 19.82 | 19.82 |
| Ethoxylated Alcohol* (100% active) | 15.00 | 10.00 | 5.00 | 0.00 |
| Ethoxylated Glycerin** (100% active) | 0.00 | 5.00 | 10.00 | 15.00 |
| TOTAL | 100.00 | 100.00 | 100.0 | 100.00 |

*The ethoxylated alcohol was Novel II 8-7 (a peaked ethoxylated alcohol where the alcohol has about 8 carbon atoms and is ethoxylated with an average of 7 moles of ethylene oxide).
**The ethoxylated glycerin was a Glycereth-26.

Figure 4:
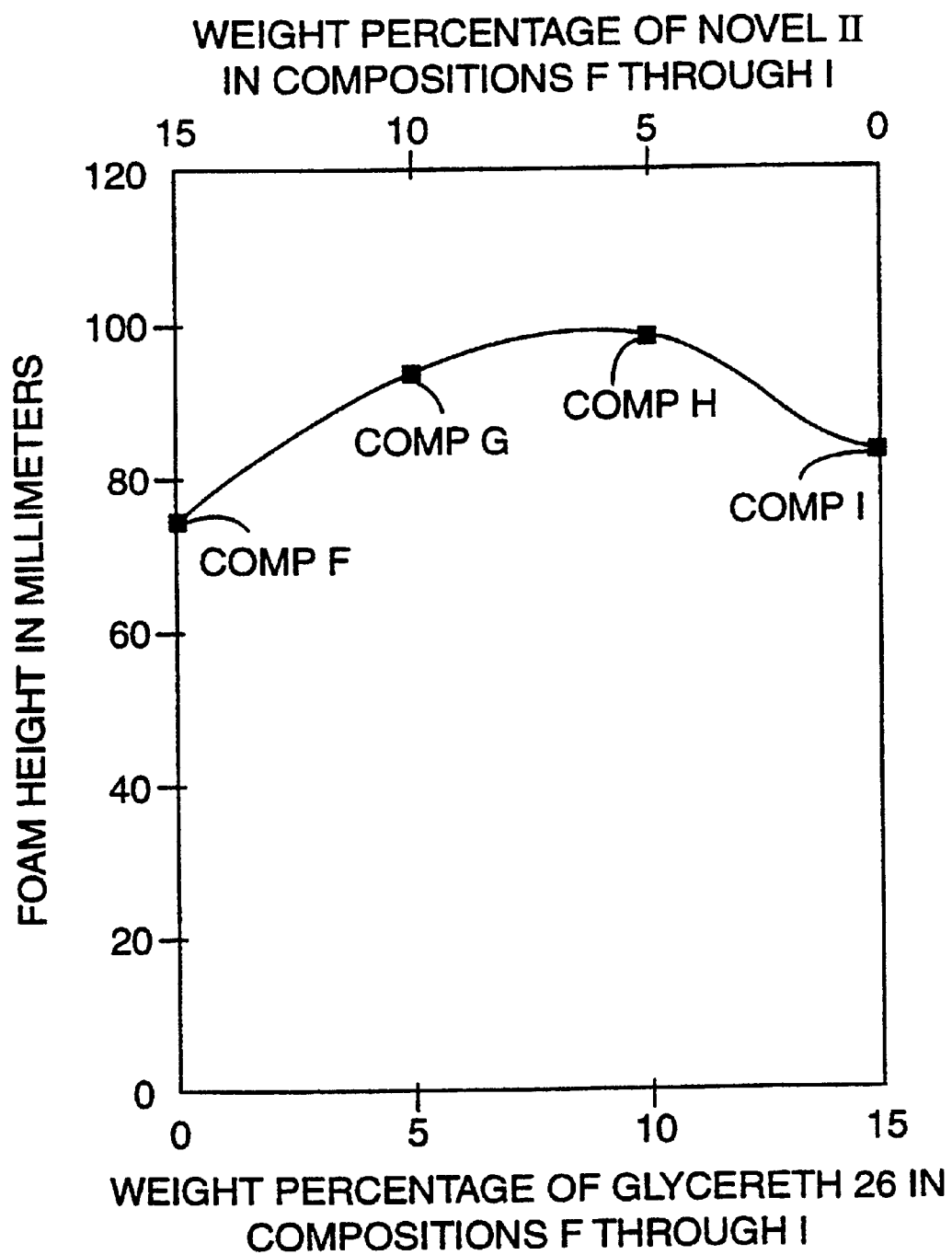
FIG. 4 shows the foam generation height of a liquid detergent that includes a hydrotrope according to the present invention, i.e., the combination of a polyethylene glycol ether of glycerin and short-chain alcohol ethoxylate at various ratios. The graph demonstrates that the presence of the hydrotrope according to the present invention results in a product that produces more foam: than would be expected by the additive effect of each of the hydrotrope constituents.

Each of the compositions was tested to determinelthe effect of the hydrotrope according to the present invention on foam generation. FIG. 4 shows that compositions containing a mixture of the alcohol ethoxylate and ethoxylated glycerin generated more foam than would have been expected: from the additive effect of each of the constituents of the hydrotrope.

In view of these results, the present invention also: contemplates a method of decreasing the viscosity of a liquid detergent, a method of increasing the rate of dissolution in an aqueous solution, and a method of increasing the foam generation ability of a liquid detergent that comprises adding an effective amount of a hydrotrope wherein the hydrotrope is a mixture of an ethoxylated alcohol and an ethoxylated glycerin, as described above. Preferably, the liquid detergent contains one or more surfactants selected from the group consisting of anionic, nonionic, amphoteric, and mixtures thereof and more preferably consists of an anionic surfactant. The liquid detergent may also include one or more foam-enhancing agents, described above.

Example 3

The following compositions were prepared:

TABLE 3

| Ingredient | J | K | L | M | N |
| --- | --- | --- | --- | --- | --- |
| Pareth 25-7 (100% active) | 46.20 | 46.20 | 46.20 | 46.20 | 46.20 |
| Alpha sulfomethyl cocoate (40% active) | 9.40 | 9.40 | 9.40 | 9.40 | 9.40 |
| Oleic acid | 9.20 | 9.20 | 9.20 | 9.20 | 9.20 |
| Triethanolamine | 4.20 | 4.20 | 4.20 | 4.20 | 4.20 |
| Citric acid | 0.07 | 0.07 | 0.07 | 0.07 | 0.07 |
| Fragrance | 0.38 | 0.38 | 0.38 | 0.38 | 0.38 |
| Water | qs to 100 | qs to ta 100 | qs to 100 | qs to 100 | qs to 100 |
| Hexylene Glycol | 4.80 | 4.80 | 4.80 | 4.80 | 4.80 |
| Ethoxylated alcohol* (100% active) | 11.60 | 5.80 | 2.90 | 1.20 | 0.00 |
| Ethoxylate Glycerin** (100% active) | 0.00 | 5.80 | 8.70 | 10.40 | 11.60 |
| TOTAL | 100.00 | 100.00 | 100.00 | 100.00 | 100.00 |

TABLE 3-continued

| Ingredient | J | K | L | M | N |
|---|---|---|---|---|---|

*The ethoxylated alcohol was Novel II 8-7 (a peaked ethoxylated alcohol where the alcohol has about 8 carbon atoms and is ethoxylated with an average of 7 moles of ethylene oxide).
**The ethoxylated glycerin was a Glycereth-26.

Figure 5:
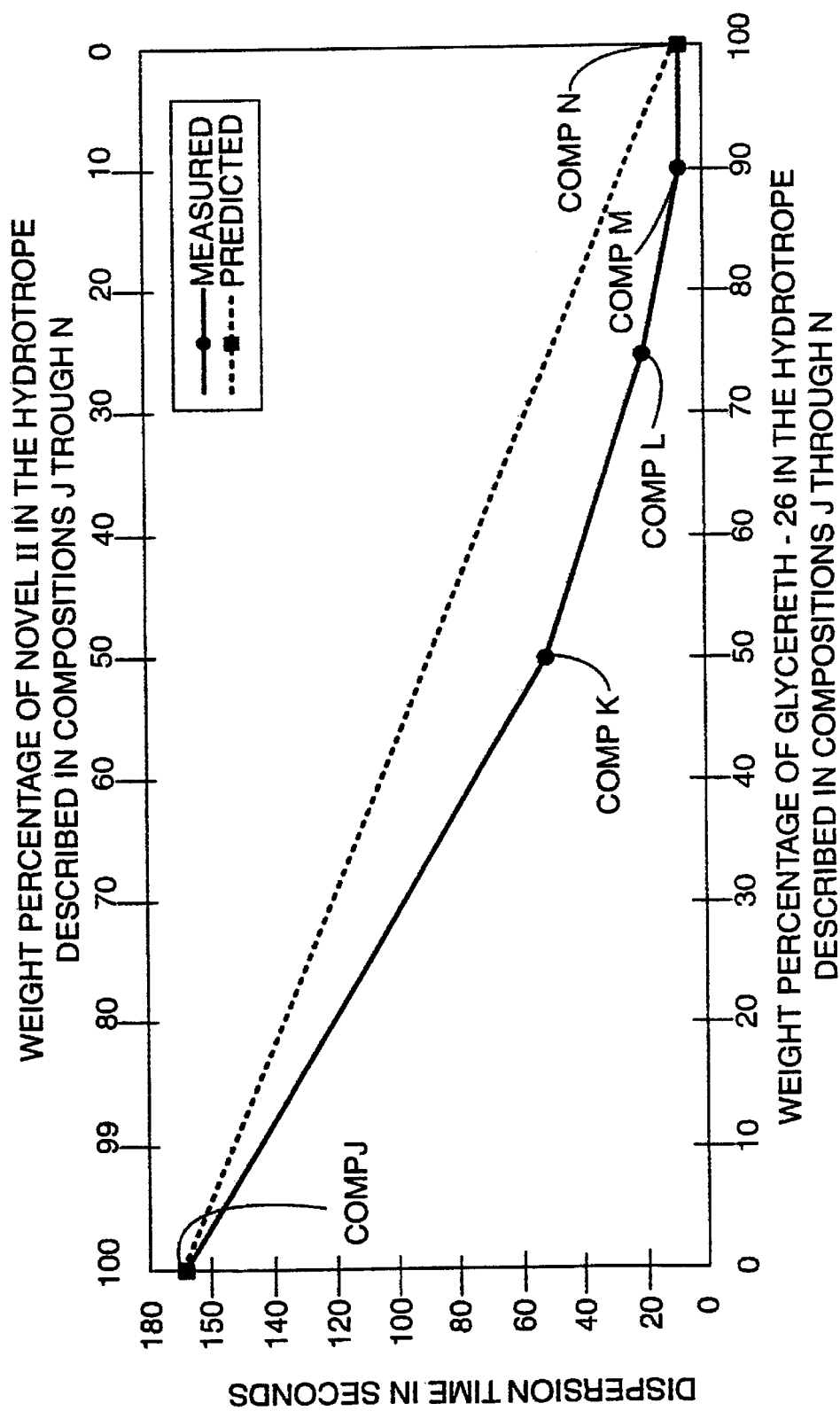
FIG. 5 shows the dissolution of a liquid detergent in water at 0° C. The liquid detergent includes a hydrotrope according to one embodiment of the present invention where the hydrotrope comprises at least about 50% of a mixture of a polyethylene glycol ether of glycerin and a short-chain alcohol ethoxylate at various ratios. The graph demonstrates that the presence of the hydrotrope according to the present invention results in a product that has better dissolution than would be expected by the additive effect of each of the hydrotrope constituents of the mixture.
Figure 6:
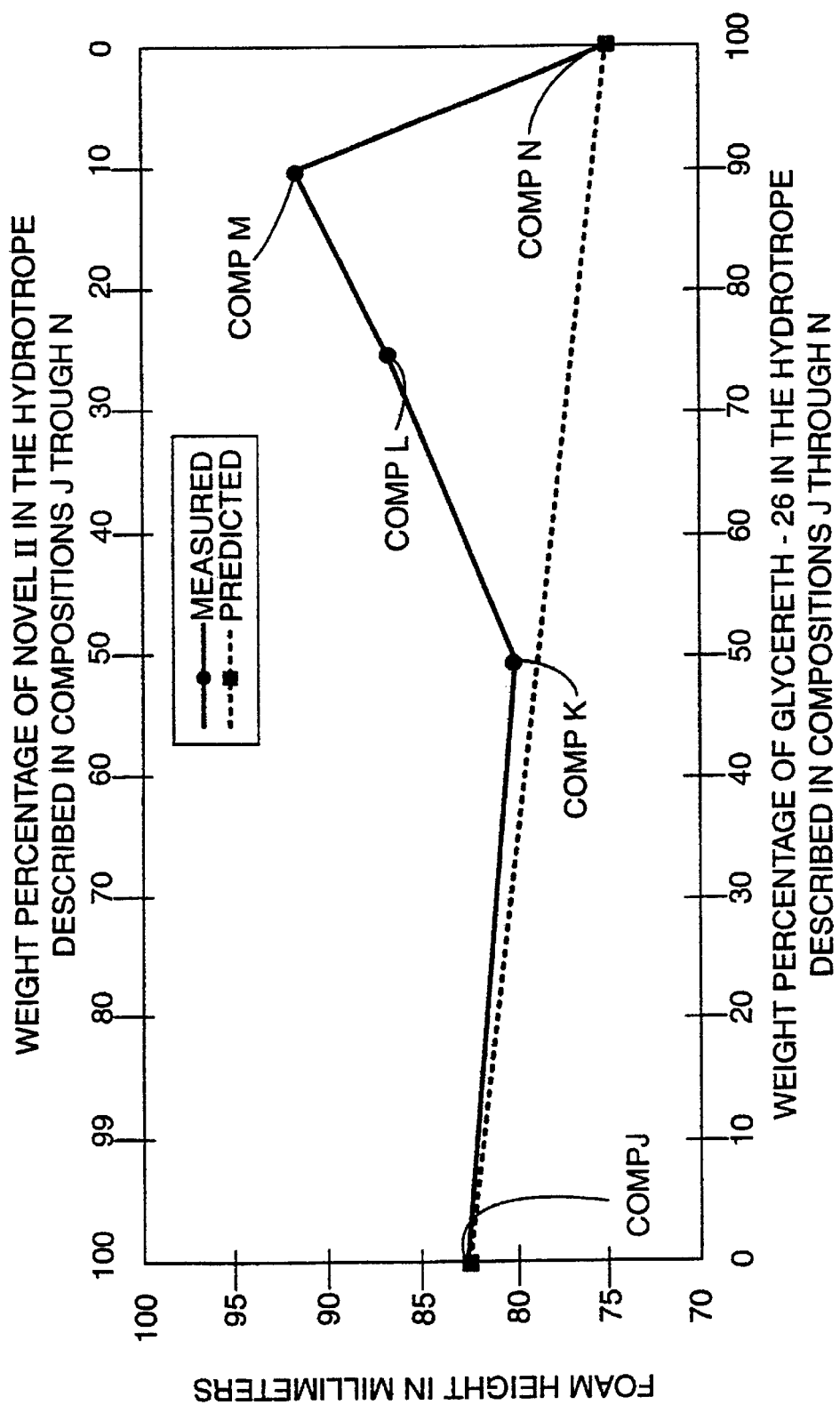
FIG. 6 shows the foam generation height of a liquid detergent that includes a hydrotrope according to one embodiment of the present invention where the hydrotrope comprises at least about 50% of a mixture of a polyethylene glycol ether of glycerin and a short-chain alcohol ethoxylate at :various ratios. The graph demonstrates that the presence of the hydrotrope according to the present invention results in a product that produces more foam than would be expected by the additive effect of each of the hydrotrope constituents of the mixture.

Each of the compositions was tested to determine the effect of the hydrotrope of the present invention on product dispersability and foam generation. FIG. 5 shows that compositions containing a mixture of the alcohol ethoxylate and ethoxylated glycerin dissolved faster in cold water than would have been expected from the additive effect of each of the constituents of the hydrotrope. FIG. 6 shows that compositions containing a mixture of the alcohol ethoxylate and ethoxylated glycerin generated more foam than would have been expected from the additive effect of each of the constituents of the hydrotrope.

Example 4

The following compositions were prepared:

TABLE 4

| Ingredient | P | Q | R | S | T |
|---|---|---|---|---|---|
| Sodium lauryl ether sulfate (60% active) | 38.80 | 38.80 | 38.80 | 38.80 | 38.80 |
| Cocamide DEA (100% active) | 18.00 | 18.00 | 18.00 | 18.00 | 18.00 |
| Cocamidopropyl amine oxide (35% active) | 13.20 | 13.20 | 13.20 | 13.20 | 13.20 |
| Citric Acid | 0.95 | 0 | 0.95 | 0 | 0.95 |
| Sulfuric Acid | 0 | 0.20 | 0 | 0.20 | 0 |
| Ethoxylated Alcohol (100% active) | 2.5* | 2.5* | 5.00** | 5.00** | 5.00** |
| Ethoxylated Glycerin*** (100% active) | 0 | 0 | 5.00 | 5.00 | 0 |
| Propylene Glycol | 5.00 | 5.00 | 0 | 0 | 0 |
| Water and other additives | Balance | Balance | Balance | Balance | Balance |
| TOTAL | 100.00 | 100.00 | 100.0 | 100.00 | 100.00 |

*The ethoxylated alcohol was Neodol 1–9 (an ethoxylated alcohol where the alcohol has about 11 carbon atoms and is ethoxylated with an average of 9 moles of ethylene oxide).
**The ethoxylated alcohol was Novel II 8-7 (a peaked ethoxylated alcohol where the alcohol has about 8 carbon atoms and is ethoxylated with an average of 7 moles of ethylene oxide).
***The ethoxylated glycerin was a Glycereth-26.

Composition R represents a preferred embodiment of the present invention.

Each composition was tested in a dermatological monitored use study to determine its health effects on human skin. In this use study, each of 104 participants were instructed to use their assigned dish soap composition (either compositions P, Q, R, S, or T as defined above) according, to usage instructions for a period of nine weeks. In general, the usage instructions were that each composition was to be used in a diluted form (1 part detergent to 7 parts water) and the participants were instructed to discontinue the use of skin lotions and to use only a mild neutral soap for personal hygiene. The skin health of each participant's hands was measured initially and at each three week interval of the nine week study. The parameters monitored were dermatological evaluation of erythema, scaling and cracking, transepidermal water loss, Nova sorption, and Desquamation index.

In general, the results of this dermatological study indicate that the use of a polyethylene glycol ether of glycerin and an alpha hydroxy acid in a liquid detergent composition synergistically combine to promote and maintain skin health when the detergent is used during washing activities. One of the tests that support this conclusion was the measurement of the transepidermal water loss. Transepidermal water loss (TEWL) is a measure of the vapor transmission barrier properties of the skin. Irritated or damaged skin will show a higher TEWL measurement than healthy skin. The mean TEWL measurements for the five compositions are shown below in Table 5:

TABLE 5

| Composition | Visit 1 Baseline | Visit 2 3 weeks | Visit 3 6 weeks | Visit 4 9 weeks | Change in TEWL From baseline to 9 weeks |
|---|---|---|---|---|---|
| P | 9.99 | 9.38 | 8.42 | 9.28 | −0.71 |
| Q | 10.55 | 11.07 | 9.23 | 10.54 | −0.04 |
| R | 13.88 | 8.30 | 10.51 | 8.69 | −5.19 |
| S | 12.48 | 11.35 | 11.15 | 9.49 | −2.99 |
| T | 9.24 | 8.00 | 7.89 | 8.54 | −0.70 |

Table 5 shows that composition R, the composition containing both the polyethylene glycol ether of glycerin (i.e. Glycereth 26) and an alpha hydroxy acid (i.e. Citric acid) showed the greatest decrease in TEWL over the 9 week period, namely −5.19 g/m$^2$/hr. Composition S, which is the same formula as composition R except without the citric acid showed the next greatest decrease in TEWL, namely −2.99 g/m$^2$/hr. Composition T, which is the same formula as composition R except without the Glycereth 26 showed a decrease in TEWL of −0.70 g/m$^2$/hr. This decrease in TEWL was comparable to composition P, which does not include both the citric acid and the Glycereth 26. This data indicates that the presence of both Glycereth 26 and citric acid contributes to the ability of the detergent composition of the present invention to improve the condition of human skin.

Another test that supports the conclusion that the combination of a polyethylene glycol ether of glycerin and an alpha hydroxy acid in a liquid detergent function to improve the skin health of the user is the Nova DPM sorption rate measurement. Nova DPM sorption rate measures the amount of water absorbed by the stratum corneum immediately after water is applied to the skin. A faster absorption rate indicates healthier skin. The net change :in Nova DPM sorption rate from the baseline measurement to the 9 week measurement is shown in Table 6.

TABLE 6

| Composition | Change in Nova DPM Sorption rate from baseline to 9 weeks |
|---|---|
| P | −0.20 |
| Q | +0.09 |
| R | +0.70 |
| S | +0.84 |
| T | +0.12 |

Table 7 shows that the compositions containing the Glycereth 26, namely compositions R and S showed the greatest increases in Nova Sorption rates. This indicates that this improvement in skin condition is attributable to the Glycereth 26.

A third test which shows that a polyethylene glycol ether of glycerin and an alpha hydroxy acid in a liquid detergent synergistically combine to improve skin health is the measurement of the Desquamation Index. The Desquamation index is a measure of the flaking of the skin. A larger number indicates an increase in fine flakes and/or course flakes of the skin. The net change in the Desquamation index from the baseline measurement to the 9 weeks !measurement is shown in Table 7.

TABLE 7

| Composition | Average change in Desquamation Index from baseline to 9 weeks |
|---|---|
| P | 5.17 |
| Q | Not available |
| R | +0.75 |
| S | 4.95 |
| T | 3.17 |

Table 8 shows that Composition R produced the smallest increase in the desquamation index. Based on these values of the desquamation index, Composition R is neither a keratolytic agent nor an irritant whereas compositions P, S, and T are mild keratolytics and cause mild irritation. These values also show that composition R showed the least increase in skin flaking ;over the course of the study.

It should be understood that a wide range of changes and modifications can be made to the embodiments described above. It is, therefore intended that the foregoing description illustrates rather than limits this invention, and that it is the following claims, including all equivalents, which define this invention.

What is claimed:

1. A method or maintaining healthy skin of a user of a liquid detergent during washing activities, the method comprising the steps of:
   a. providing a liquid detergent that includes a polyethylene glycol ether of glycerin, an ethoxylated alcohol, and an alpha hydroxy acid, the polyethylene glycol ether of glycerin having the formula:

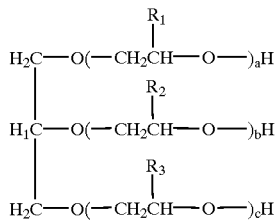

wherein a+b+c has an average value of from about 2 to about 60, and wherein $R_1$, $R_2$, and $R_3$ may be the same or different and are selected from the group consisting of H, $CH_3$, and $C_2H_5$;
   b. diluting the liquid detergent in water external to the liquid detergent; and
   c. using the liquid detergent and external water to wash the desired object, whereby the health of the user's skin is maintained during the washing activity.

2. The method of claim 1 wherein a+b+c has an average value of from about 20 to about 30.

3. The method of claim 1 wherein the polyethylene glycol ether of glycerin is Glycereth-26.

4. The method of claim 1 wherein the alpha hydroxy acid is selected from the group consisting of citric acid, malic acid, lactic acid, glycolic acid, tartartic acid, tartronic acid, and glucuronic acid.

5. The method of claim 1 wherein the alpha hydrqoxy acid is citric acid.

6. The method of claim 1 wherein the liquid detergent further includes a peaked ethoxylated alcohol where the alcohol has from about 6 Carbon atoms to about 12 Carbon atoms and is ethoxylated with an average of from about 3 moles of ethylene oxide to about 9 moles of ethylene oxide.

7. A method of improving the skin of a user of a liquid detergent during washing activities, the method comprising the steps of:
   a. providing a liquid detergent that includes a polyethylene glycol ether of glycerin, an ethoxylated alcohol, and an alpha hydroxy acid, the-polyethylene glycol ether of glycerin having the formula:

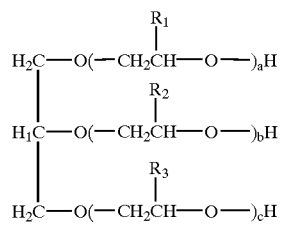

wherein a+b+c has an average value of from about 2 to about 60, and wherein $R_1$, $R_2$, and $R_3$ may be the same or different and are selected from the group consisting of H, $CH_3$, and $C_2H_5$;
   b. diluting the liquid detergent in water external to the liquid detergent; and
   c. using the liquid detergent and external water to wash the desired object, whereby the health of the user's skin is improved during the washing activity.

8. The method of claim 7 wherein a+b+c has an average value of from about 20 to about 30.

9. The method of claim 7 wherein me polyethylene glycol ether of glycerin is Glycereth-26.

10. The method of claim 7 wherein the alpha hydroxy-:acid is selected from the group consisting of citric acid, matic acid, lactic acid, glycolic acid, tartartic acid, tartronic acid, and glucuronic acid.

11. The method of claim 7 wherein the alpha hydroxy acid is citric acid.

12. The method of claim 7 wherein the liquid detergent further includes a peaked ethoxylated alcohol where the alcohol has from about 6 Carbon atoms to about 12 Carbon atoms and is ethoxylated with an average of from about 3 moles of ethylene oxide to about 9 moles of ethylene oxide.

\* \* \* \* \*